United States Patent [19]

Ratton

[11] Patent Number: 4,738,796

[45] Date of Patent: Apr. 19, 1988

[54] PROCESS FOR PREPARING ORGANIC COMPOUNDS CONTAINING AN ALKOXYALKYLIDENE GROUP

[75] Inventor: Serge Ratton, Villefontaine, France

[73] Assignee: Rhone-Poulenc Specialites Chimiques, Courbevoie, France

[21] Appl. No.: 748,457

[22] Filed: Jun. 25, 1985

[30] Foreign Application Priority Data

Jun. 25, 1984 [FR] France ................................ 84 10182

[51] Int. Cl.$^4$ ...................... C09K 15/20; C09K 15/32; C07C 69/73
[52] U.S. Cl. .................................. 252/400.2; 252/402; 252/403; 560/2; 560/181
[58] Field of Search ...................... 252/402, 400.2, 403; 560/2, 181

[56] References Cited

U.S. PATENT DOCUMENTS

| | | | |
|---|---|---|---|
| 2,676,926 | 4/1954 | Smith et al. .................. | 252/403 X |
| 2,824,121 | 2/1958 | Nicholl et al. . | |
| 3,118,949 | 1/1964 | Cull et al. . | |
| 3,376,232 | 4/1968 | Coover, Jr. et al. .............. | 252/400.2 |
| 3,489,722 | 1/1970 | Kotani et al. .................. | 560/2 X |
| 4,058,553 | 11/1977 | Ackermann et al. . | |
| 4,665,218 | 5/1987 | Englaender et al. ................ | 560/181 |

FOREIGN PATENT DOCUMENTS 0168305 1/1986 European Pat. Off. ................ 560/2
41-4776 3/1966 Japan .

OTHER PUBLICATIONS

Sah, Condensation of Ortho Esters with Acetoacetic Ester and Malonic Ester, J. Am. Chem. Soc., 53, 1836 (1931).
Post and Erickson, The Reactions of Ortho Esters with Certain Acid Anhydrides, J. Org. Chem. 2, 260 (1937).
Fuson, Parham and Reed, Alkylation of Ethyl Malonate with Diethoxymethyl Acetates, J. Org. Chem. 11, 194 (1946).

*Primary Examiner*—John F. Terapane
*Assistant Examiner*—John S. Maples
*Attorney, Agent, or Firm*—Finnegan, Henderson, Farabow, Garrett & Dunner

[57] ABSTRACT

Process for the heat stabilization of alkyl alkoxyalkylidenemalonates in the presence of Lewis acids, such as metal catalytic compounds employed as catalysts during the preparation of the alkyl alkoxyalkylidenemalonates by condensation of a suitable malonate with a suitable ortho ester. The condensation reaction mixture is heated in the presence of a stabilizing compound selected from the group consisting of 8-hydroxyquinolines and organic acid phosphates in an amount sufficient to stabilize the alkyl alkoxyalkylidenemalonates against thermal decomposition.

8 Claims, No Drawings

PROCESS FOR PREPARING ORGANIC COMPOUNDS CONTAINING AN ALKOXYALKYLIDENE GROUP

The present invention relates to a process for preparing alkyl alkoxyalkylidenemalonates by condensation of an ortho ester with an alkyl malonate.

The organic compounds containing an alkoxyalkylidene group corresponding to the general formula:

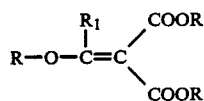

in which R denotes an alkyl radical, $R_1$ a hydrogen atom, an alkyl radical or a phenyl group, are intermediates which are especially sought after in organic synthesis. For example, alkyl alkoxymethylenemalonates are employed to obtain alkyl anilinomethylenemalonates which are intermediates in the synthesis of substituted quinolines such as 4,7-dichloroquinoline or 4-chloro-7-trifluoromethylquinoline (cf. French Pat. No. 950,883).

Particularly preferred are alkyl alkoxyalkylidenemalonates of the formula:

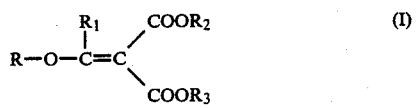

in which:

R denotes an alkyl radical containing 1 to 4 carbon atoms, preferably a methyl or ethyl radical;

$R_1$ denotes a hydrogen atom or a methyl, ethyl or phenyl radical; and $R_2$ and $R_3$, which may be identical to or different from both each other and R, denote alkyl radicals containing 1 to 4 carbon atoms, preferably methyl or ethyl radicals.

It is well-known that alkyl alkoxyalkylidenemalonates are obtained by condensation of a suitable alkyl malonate, such as ethyl malonate, with a suitable ortho ester, such as alkyl (particularly methyl or ethyl) orthoformates, orthoacetates and orthobenzoates. See, e.g., L. Claisen, Ber. 26 page 2729 et seq. (1893) and Ann. 297 page 16 et seq. (1897); P. Sah, J. Am. Chem. Soc. 53 page 1836 et seq. (1931). One skilled in the art can readily select suitable alkyl malonates and ortho esters for this well-known condensation, which can be represented by the following reaction scheme:

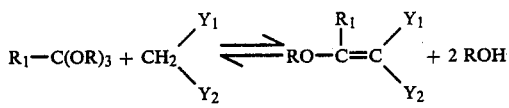

where $Y_1$ and $Y_2$ are COO alkyl.

This condensation is generally carried out in the presence of zinc chloride as a catalyst and acetic anhydride as a condensing agent. This reaction has been subject of various investigations into its mechanism [cf. H. W. Post et al, J. Org. Chem. 2 page 260 et seq. (1937) and R. C. Fuson et al. J. Org. Chem. 11 page 194 et seq. (1946)], especially with the aim of improving the yields of alkoxymethylenemalonates (cf. R. C. Fuson et al, loc. cit.).

Various improvements to the Claisen process have been proposed subsequently with the aim of raising the yields of alkyl alkoxymethylenemalonates (in particular in relation to the orthoformates) and the productivity of the reaction. In U.S. Pat. No. 2,824,121 it has been proposed to carry out the condensation in the absence of zinc chloride, to replace acetic anhydride with a quantity of acetic acid which is insufficient to convert the alcohol formed during the reaction to the corresponding acetate and to remove the alcohol by distillation as it is formed. Despite the improved results which it has produced, this process has not led to adequate yields as far as the orthoformate is concerned.

In Japanese Patent Application published under No. 4776/66 it was recommended to operate in the presence of metal catalysts (zinc and iron salts) in the absence of acid or anhyride and in a hydrocarbon solvent (benzene, xylene, toluene) while ensuring the removal of the alcohol formed by azeotropic distillation. It has not been possible to confirm the yields claimed for this process.

Lastly, in French Patent Application No. 75/17,177, published under No. 2,273,793, it has been proposed to prepare alkyl alkoxymethylenemalonates by reacting an alkyl malonate with an excess of alkyl orthoformate at 100°-160° C., in the presence of a zinc, aluminum or iron salt and by removing the alcohol resulting from the condensation as it is formed. Despite the improvement in the yields which it contributes, this process does not make it possible to exceed an alkoxymethylenemalonate yield of 90% of theory based on the orthoformate.

It has been found that the catalysts employed to promote the course of the reaction, and particularly cadmium, magnesium, bismuth and mercury, use of which was recommended in French Patent Application No. 84/02,027 of Feb. 7, 1984 and corresponding co-pending U.S. Application Ser. No. 698,371, filed on Feb. 1, 1985 now abandoned, and zinc promote the decomposition of alkyl alkoxyalkylidenemalonates when they are distilled to separate them from the reaction medium and to purify them. The extent of decomposition is naturally a function of distillation conditions and depends particularly on the temperature to which the crude condensation mixture is heated and on the distillation time. The extent of this decomposition also depends directly on the quantity of catalyst.

In general, the decomposition can reach from 2 to 5% by weight of the alkoxyalkylidenemalonate produced during the condensation. However, during distillation on an industrial scale, which requires a high reflux ratio to ensure excellent purity of the product, and consequently prolonged distillation times, the extent of the decomposition of the required product can reach maximum values of the order of 10%.

To avoid this harmful effect of the catalyst on the stability of the alkoxyalkylidenemalonates when heated, the catalyst should be removed from the reaction mixture before distillation [cf. French Patent Application No. 75/17,177, published under No. 2,273,793]. French Patent Application No. 75/17,177 teaches furthermore that the yields of ethyl ethoxymethylenemalonate decrease when the quantity, and hence the concentration, of Lewis acid in the medium increases, which is precisely the case during distillation. This removal of the catalyst involves either filtration of the entire reaction mixture without complete removal of all the catalyst (a part remains dissolved in the medium), or washing the reaction mixture with acidified water, which is a complex operation that can result in loss of initial reactants and/or of alkoxyalkylidenemalonate by hydrolysis.

An object of the present invention is to solve the problem presented by the distillation of alkyl alkoxyalkylidenemalonates in the presence of catalysts of the Lewis acid type which are employed during the Claisen condensation between suitable ortho esters and alkyl malonates. More generally, the present invention seeks to inhibit or restrict the harmful effect of Lewis acids in general and particularly of zinc, magnesium, cadmium, bismuth and mercury compounds, such as salts, for example, halides or carboxylates, on the thermal stability of alkyl alkoxyalkylidenemalonates.

More specifically, the subject of the present invention is a process for heat stabilization of alkyl alkoxyalkylidenemalonates in the presence of a metal compound employed in a catalytically effective amount during the preparation of the alkoxyalkylidenemalonates by condensation of a suitable malonate with a suitable ortho ester. In this process, the alkoxyalkylidenemalonate and the metal compound are heated in the presence of a stabilizing compound selected from the group consisting of 8-hydroxyquinolines and organic acid phosphates in an amount sufficient to stabilize the alkoxyalkylidenemalonate against thermal decomposition.

The present invention also comprehends a mixture comprising an alkyl alkoxyalkylidenemalonate, a Lewis acid, such as a metal catalytic compound, and a compound selected from the group consisting of 8-hydroxyquinolines and organic acid phosphates in an amount sufficient to stabilize the alkoxyalkylidenemalonate against thermal decomposition.

The process according to the invention makes it possible to subject directly to distillation, after the addition of an effective quantity of an 8-hydroxyquinoline or of an organic acid phosphate (both of which are sometimes called stabilizers hereafter), the reaction mixture resulting from the condensation, in the presence of Lewis acids and particularly metal catalytic compounds, of suitable ortho esters with suitable alkyl malonates. As explained above, the distillation separates the excess ortho ester from the alkyl alkoxyalkylidenemalonate.

A second object of the present invention is consequently a process for heat stabilization of alkyl alkoxyalkylidenemalonates and in particular of mixtures containing suitable alkyl ortho esters, alkyl alkoxyalkylidenemalonates and Lewis acids, such as metal catalytic compounds, which are to be distilled. The heating or distillation is carried out in the presence of an effective quantity of a stabilizing compound selected from the group consisting of 8-hydroxyquinolines and organic acid phosphates.

Preferred organic acid phosphates include compounds of the general formula:

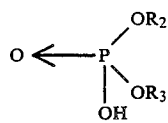

in which $R_2$ denotes a hydrocarbon radical containing from 1 to 20 carbon atoms and $R_3$ a hydrogen atom or a hydrocarbon radical containing from 1 to 20 carbon atoms and wherein $R_2$ and $R_3$ can be identical or different.

More preferably, $R_2$ and $R_3$ represent alkyl radicals containing from 1 to 20 carbon atoms, such as methyl, ethyl, n-propyl, isopropyl, n-butyl, t-butyl, amyl, n-pentyl, 2-ethylhexyl, n-hexyl, n-octyl, dodecyl, and octadecyl; cycloalkyl radicals optionally substituted by lower alkyl radicals (preferably containing from 1 to 4 carbon atoms), the cycloalkyl radicals containing from 5 to 12 ring carbon atoms, such as cyclopentyl, cyclohexyl, cycloheptyl and cyclodecyl radicals; and arylalkyl radicals containing from 1 to 12 carbon atoms in the alkyl moiety, such as benzyl or B-phenylethyl radicals.

Specific examples of phosphates which can be employed in the present process include methyl phosphate, dimethyl phosphate, ethyl phosphate, diethyl phosphate, and di-n-propyl, di-n-butyl, diisobutyl, cyclohexyl, dicyclohexyl, benzyl, and B-phenylethyl phosphates. The phosphates may be employed in the form of mixtures of organic mono-, di- or triphosphates with, optionally, residual quantities of phosphoric acid, such as those produced by the esterification of alcohols with phosphoric acid. The presence of a triphosphate, which may not contribute to the heat stabilizing objective, is acceptable.

Any 8-hydroxyquinoline may be employed in the process of the invention. Preferably, use is made of compounds of the formula:

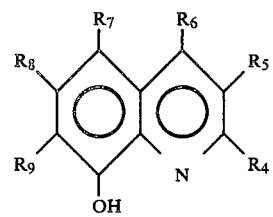

in which $R_4$ to $R_9$, which are identical or different, denote a hydrogen atom or hydrocarbon radicals containing from 1 to 20 and preferably from 1 to 12 carbon atoms, a halogen atom, an $-SO_3H$, $-NO_2$ or carboxy group. More preferably, $R_4$ to $R_9$ denote an alkyl radical containing from 1 to 20 carbon atoms, such as methyl, ethyl, n-propyl, isopropyl, n-butyl, isobutyl, n-pentyl, n-hexyl, n-heptyl, 2-ethylhexyl, octyl or decyl radicals; a cycloalkyl radical optionally substituted by 1 to 3 lower alkyl radicals, such as cyclopentyl, cyclohexyl, methylcyclohexyl or ethylcyclohexyl; an aryl radical optionally substituted by 1 to 3 lower alkyl radicals, such as phenyl, toluyl or xylyl radicals; an arylalkyl radical containing from 1 to 4 carbon atoms in the alkyl moiety, such as benzyl or B-phenylethyl radical; a halogen atom such as fluorine, chlorine or bromine; and a linear or branched alkenyl radical containing from 2 to 20 carbon atoms and one or more ethylenic double bonds, such as vinyl, 2-propenyl, 2-butenyl, isobutenyl, or 3,3,5,5,-tetramethyl-1-vinylhexyl. The sum of the carbon atoms in the various substituents $R_4$ to $R_9$ preferably does not exceed 20 and up to three of the radicals $R_4$ to $R_9$ may denote an $-SO_3H$, $-NO_2$ or $-COOH$ group or a halogen atom.

Representative examples of 8-hydroxyquinolines are 8-hydroxyquinoline, 2-methyl-8-hydroxyquinoline, 3-ethyl-8-hydroxyquinoline, 6-ethyl-8-hydroxyquinoline, 2-isopropyl-8-hydroxyquinoline, 7-n-pentyl-8-hydroxyquinoline, 2-cyclohexyl-8-hydroxyquinoline, 2-phenyl-8-hydroxyquinoline, 3-benzyl-8-hydroxyquinoline, 5,7-dichloro-2-methyl-8-hydroxyquinoline, 5-chloro-8-hydroxyquinoline, 5-chloro-2-methyl-8-hydroxyquinoline, 5,6,7-trichloro-8-hydroxyquinoline, 5,7-dibromo-8-hydroxyquinoline, 5,7-dibromo-2-methyl-8-hydroxyquinoline, 5-sulfonyl-8-hydroxyquinoline, 7-sulfonyl-8-hydroxyquinoline, 5-nitro-8-hydroxyquinoline, 2-methyl-5-nitro-8-hydroxyquinoline, 2-chloro-5-nitro-8-hydroxyquinoline, 5-carboxy-8-hydroxyquinoline and 2-(3,3,5,5-tetramethyl-1-vinylhexyl)-8-hydroxyquinoline.

The quantity of stabilizer depends on the nature and the quantity of the Lewis acid, such as a metal catalytic compound, present in the alkyl alkoxyalkylidenemalonate and/or in the mixture produced by the Claisen condensation, and on the nature of the stabilizer. One skilled in the art can determine the appropriate quantity by means of simple tests similar to the tests utilized in the following examples, in each individual case without engaging in undue experimentation. In general, this quantity, expressed in moles of stabilizer per mole of Lewis acid, is at least about 0.8 mole, preferably at least 1 mole, per mole. There is no critical upper limit to the quantity of stabilizer; however, in practice there is no advantage in using more than 10 moles stabilizer per mole of Lewis acid.

The process according to the invention is especially suitable for the distillation of mixtures produced by the condensation of a suitable alkyl malonate with an excess of a suitable alkyl orthoformate in the presence of at least one Lewis acid usually employed in the Claisen condensation. Lewis acids particularly contemplated are metal catalytic compounds including zinc salts, such as zinc chloride, zinc acetate, zinc propionate or cadmium, magnesium, bismuth and mercury salts, such as halides, sulfates, nitrates, carbonates, phosphates, carboxylates and sulfonates. For practical reasons, use is preferably made of the halides (more preferably chlorides and bromides) and carboxylates.

In the case of carboxylates, use can be made of the Cd, Hg, Bi and Mg salts of any carboxylic acid, such as saturated or unsaturated aliphatic, alicyclic or aromatic mono- or polycarboxylic acids. Salts of formic, acetic, propionic, butyric, pentanoic, hexanoic, octanoic, dodecanoic, hexadecanoic, stearic or oleic acids, salts of mixtures of fatty acids such as naphthenic acid, salts of the acid sold under the trade name "Versatic acid", and salts of benzoic acid, are particularly preferred.

In practice, use is preferably made of the chlorides and bromides of Cd, Hg, Bi and Mg and of the carboxylates of lower aliphatic acids. Illustrative compounds include cadmium chloride, cadmium bromide, magnesium chloride and bromide, mercuric chloride and bromide, bismuth chloride ($BiCl_3$) and bismuth bromide ($BiBr_3$), cadmium acetate [$Cd(C_2H_3O_2)_2$], cadmium benzoate, cadmium oxalate, cadmium salicylate, bismuth acetate [$Bi(C_2H_3O_2)_2$], bismuth benzoate, mercuric acetate [$Hg(C_2H_3O_2)_2$], mercuric benzoate, mercuric oxalate, magnesium acetate, magnesium benzoate, magnesium laurate, magnesium oxalate, magnesium palmitate and magnesium stearate.

The following examples illustrate the invention and show how it can be employed in practice.

EXAMPLES 1 TO 3

Into a 100 ml round glass flask fitted with a thermometer, a vertical condenser and a heating system are charged 53.3 g of ethyl ethoxymethylenemalonate, various quantities of stabilizer, and 800 ppm (parts per million by weight) of $ZnCl_2$. The contents of the flask are then heated to 155° C. and kept at this temperature for 8 hours. For comparison, the same experiment is carried out in the absence of inhibitor, and in the presence and absence of $ZnCl_2$. After the contents of the flask have cooled, ethyl ethoxymethylenemalonate is determined by gas phase chromatography.

The results obtained are listed in the following table:

| | STABILIZER | | EEMM (1) RECOVERED | |
|---|---|---|---|---|
| | NATURE | QUANTITY in g | IN WEIGHT | IN % (2) |
| EX. | | | | |
| 1 | diethyl acid phosphate (3) | 0.36 | 52.74 | 99 |
| 2 | 8-hydroxyquinoline | 0.44 | 53.3 | 100 |
| 3 | 8-hydroxyquinoline | 0.177 | 52.05 | 97.7 |
| CONTROL TESTS | | | | |
| A (4) | none | | 48.77 | 91.5 |
| B (5) | none | | 53.3 | 100 |

(1) EEMM is an abbreviation for ethyl ethoxymethylenemalonate
(2) relative to the EEMM charged
(3) mixture containing 1.5 mol % of $H_3PO_4$, 45.2% of monoethyl phosphate; 45.7% of diethyl phosphate, 1.8% of trimethyl phosphate and 5.7% of pyrophosphates.
(4) test made in the presence of $ZnCl_2$
(5) test made in the absence of $ZnCl_2$ Comparison of test A with test B shows that $ZnCl_2$ is responsible for the decomposition of 8.5% of ethyl ethoxymethylenemalonate and comparison of Examples 1 to 4 demonstrates the advantageous effect the stabilizers of the present invention have on the harmful effect of $ZnCl_2$.

EXAMPLE 4

Into a stainless steel boiler of a 1.5 liter capacity, equipped with a thermometer, a stainless steel column with 5 to 7 theoretical plates, and connected to a vacuum pump, are charged 500 g of diethyl ethoxymethylenemalonate, 1.344 g of zinc acetate dihydrate and 4.44 of 8-hydroxyquinoline. Distillation of the ethoxymethylenemalonate is then carried out at a pressure reduced to 38–40 mm of mercury. The distillation takes 8 hours, in the course of which there are collected: a first fraction of 11.4 g containing 94.5% of EEMM, a second fraction of 451.1 g containing 100% of EEMM, a third fraction of 18.9 g containing 98.3%, and a residue of 10.2 g containing 93% of EEMM. In all, 98% of the EEMM charged (490 g) has been recovered.

For comparison, the distillation was repeated in the absence of 8-hydroxyquinoline and in the presence of zinc chloride (Test C) and in the absence of zinc acetate and of stabilizer (Test D). The results obtained are listed in the following table:

| | | TEST C | TEST D |
|---|---|---|---|
| FRACTION 1 | Quantity in g | 11.9 | 8.3 |
| | % of EEMM by weight | 95.2 | 90.3 |
| FRACTION 2 | Quantity in g | 432.8 | 466.7 |
| | % of EEMM by weight | 99.3 | 100 |
| FRACTION 3 | Quantity in g | 28 | |
| | % of EEMM by weight | 97 | |
| RESIDUE | Quantity in g | 14.7 | 17 |
| | % of EEMM by weight | 62.6 | 93 |
| TOTAL EEMM | in weight | 477.4 | 490 |
| RECOVERED | in % | 95.4 | 98 |

EXAMPLE 5

The process was carried out as in Example 1 by heating, for 7 hours, 30 minutes at 157° C., 54.12 g of ethyl ethoxymethylenemalonate containing 0.167 g of cadmium acetate dihydrate and 0.36 g of the diethyl phosphate defined in Example 1.

After heating had been stopped, 53.7 g of EEMM, i.e., 99.2% of the original quantity, were determined.

For comparison, this example was reproduced in the absence of phosphate. 52.14 g of EEMM were determined out of 54.54 g charged, i.e., 95.6% of the original quantity.

EXAMPLE 6

The process was carried out as in Example 1 by heating, for 7 hours 30 minutes at 155° C., 53.29 g of ethyl ethoxymethylenemalonate containing 0.412 g of $MgCl_2.6H_2O$ and 1.16 g of the diethyl phosphate defined in Example 1.

After heating had been stopped, 48.92 g of EEMM, i.e., 91.8% of the original quantity, were determined.

For comparison, this Example was reproduced in the absence of phosphate. 37.1 g of EEMM were determined out of 52.54 g charged, i.e., 70.6% of the original quantity.

I claim:

1. A mixture comprising an alkyl alkoxyalkylidenemalonate, a Lewis acid and a compound selected from the group consisting of 8-hydroxyquinolines and organic acid phosphates in an amount sufficient to stabilize said alkoxyalkylidenemalonate against thermal decomposition.

2. The mixture of claim 1, wherein said Lewis acid is a metal catalytic compound selected from the group consisting of zinc, magnesium, cadmium, bismuth and mercury compounds.

3. The mixture of claim 1, wherein said organic acid phosphate is of the formula:

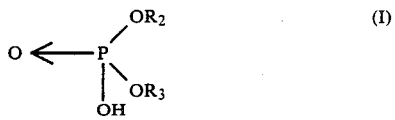

in which $R_2$ and $R_3$ independently denote a hydrocarbon radical containing from 1 to 20 carbon atoms and in which $R_3$ may also be a hydrogen atom.

4. The mixture of claim 3, wherein said stabilizing compound is a mixture of monoethyl phosphate and diethyl phosphate.

5. The mixture of claim 3, wherein said stabilizing compound is diethyl phosphate.

6. The mixture of claim 1, wherein said 8-hydroxyquinoline is of the formula:

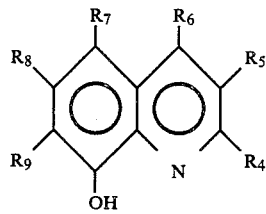

in which $R_4$ to $R_9$, which are identical or different, are selected from the group consisting of a hydrogen atom, a hydrocarbon radical containing from 1 to 20 carbon atoms, a halogen atom, an $-SO_3H$ group, a $-NO_2$ group and a $-COOH$ group.

7. The mixture of claim 6, wherein said stabilizing compound is 8-hydroxyquinoline.

8. The mixture of claim 6, wherein the sum of the carbon atoms in substituents $R_4$ to $R_9$ does not exceed 20 and up to three of the radicals $R_4$ to $R_9$ may be an $-SO_3H$ group, a $-NO_2$ group, a $-COOH$ group or a halogen atom.

* * * * *